US011096580B2

(12) United States Patent
Mukherjee et al.

(10) Patent No.: US 11,096,580 B2
(45) Date of Patent: Aug. 24, 2021

(54) ADAPTIVE HEALTH SCORE

(71) Applicant: Covidien LP, Mansfield, MA (US)

(72) Inventors: Amit Mukherjee, Elkridge, MD (US); Shashidhar Yamsani, Annapolis, MD (US); Ankita Mishra, Crofton, MD (US); Pooja Duggappa Balegar, Annapolis, MD (US)

(73) Assignee: Covidien LP, Mansfield, MA (US)

( * ) Notice: Subject to any disclaimer, the term of this patent is extended or adjusted under 35 U.S.C. 154(b) by 176 days.

(21) Appl. No.: 16/246,271

(22) Filed: Jan. 11, 2019

(65) Prior Publication Data

US 2019/0223724 A1 Jul. 25, 2019

Related U.S. Application Data

(60) Provisional application No. 62/621,736, filed on Jan. 25, 2018.

(51) Int. Cl.
*A61B 5/00* (2006.01)
*G16H 50/00* (2018.01)
*G16H 50/30* (2018.01)
*A61B 5/0205* (2006.01)

(52) U.S. Cl.
CPC .......... *A61B 5/0022* (2013.01); *A61B 5/7275* (2013.01); *A61B 5/7282* (2013.01); *G16H 50/30* (2018.01); *A61B 5/0006* (2013.01); *A61B 5/0008* (2013.01); *A61B 5/02055* (2013.01)

(58) Field of Classification Search
CPC .... G16H 50/30; A61B 5/0022; A61B 5/7275; A61B 5/7282
See application file for complete search history.

(56) References Cited

U.S. PATENT DOCUMENTS

| 2017/0113050 | A1* | 4/2017 | Brisben | A61N 1/3925 |
| 2018/0247713 | A1* | 8/2018 | Rothman | G16H 50/30 |
| 2020/0253537 | A1* | 8/2020 | Blount | A61B 5/7275 |

FOREIGN PATENT DOCUMENTS

WO   WO-2018125077 A1 *  7/2018  .......... A61B 5/0024

* cited by examiner

*Primary Examiner* — Allen Porter
*Assistant Examiner* — Adreanne A. Arnold
(74) *Attorney, Agent, or Firm* — Holland & Hart LLP

(57) ABSTRACT

Methods, systems, and devices for determining an adaptive health score are described. Methods may include receiving physiological information at a medical device and determining first and second patient health scores based in part on historical patient data and data associated with a larger population. The method may also include assigning complimentary first and second weighted values to the respective scores and, ultimately, determining an adaptive health score for the patient. In addition the method may update, or calculate a new adaptive health score, based on predetermined time intervals, or changes in the type or quantity of physiological data.

12 Claims, 10 Drawing Sheets

ADAPTIVE HEALTH SCORE

CROSS REFERENCES

The present Application for Patent claims priority U.S. Provisional Patent Application No. 62/621,736 by Mukherjee et al., entitled "ADAPTIVE HEALTH SCORE", filed Jan. 25, 2018, assigned to the assignee hereof.

BACKGROUND

The following relates generally to determining an adaptive health score associated with a patient.

In a healthcare facility such as a hospital, physiological parameters of the patient (e.g., heart rate, respiratory rate, blood pressure) may be monitored by one or more medical devices. The medical devices may be battery powered and may wirelessly transmit measured patient data over a wireless network within the hospital, thereby allowing the patient to move freely through the hospital while being monitored. Clinicians may remotely monitor the patient by accessing the patient data at a central nurse station or on any web enabled device connected to the network (e.g., smartphone or tablet).

In some cases, patient monitoring devices may provide instantaneous patient health scores based on the patient's condition at a specific time. Consequently, the patient's health may not be comprehensively assessed based on his or her medical history, which may result in an inaccurate or incomplete assessment of the patient. While clinicians may attempt to assess a patient's condition at a specific time based on his or her medical history, the assessment may be both time consuming and highly-complex based on the amount of historical patient data readily available. Therefore, improvements in adaptive patient monitoring are desired.

SUMMARY

The described features generally relate to methods, systems, devices, or apparatuses that support determining an adaptive health score associated with a patient. A medical device may receive first physiological data associated with a patient. Upon receiving the first physiological data associated with the patient, the medical device may determine a first patient health score, the first patient health score determination comprising calculating a difference between at least one characteristic of the first physiological data and at least one characteristic of historic physiological data associated with the patient. The medical device may then determine a second patient health score, the second patient health score determination comprising calculating a difference between the at least one characteristic of the first physiological data and at least one characteristic of population physiological data associated with a population of patients, wherein each of the patient and the population of patients comprise at least one similar biological, environmental, or behavioral characteristic. Upon determining the second patient health score, the medical device may assign a first weighted value to the first patient health score as a function of an amount of the historic physiological data and assign a second weighted value to the second patient health score as a compliment function of the first weighted value. The medical device may then determine the adaptive health score based at least in part on the assigning of the first and second weighted values.

Methods and apparatuses are described for determining an adaptive health score associated with a patient. A method may include re-assigning the first weighted value and the second weighted value to each of the first patient health score and the second patient health score based at least in part on a change in the first physiological data. Additionally, the method may include re-determining the adaptive health score based at least in part on the re-assignment of the first weighted value and the second weighted value. In some examples, the method may include receiving the first physiological data associated with the patient at a first time and receiving the first physiological data associated with the patient at a second time different from the first time, wherein the re-assignment of the weighted value to the first patient health score and the second patient health score is based at least in part on a change in the first physiological data from the first time to the second time.

In some examples, the method may further include receiving, at the medical device, second physiological data associated with the patient that is different from the first physiological data, wherein the determination of the first patient health score and the second patient health score are based at least in part on the second physiological data received. Additionally, the method may include aggregating the adaptive health score with one or more additional adaptive health scores to form an aggregated adaptive health score, wherein the one or more additional adaptive health scores are determined using a same type of first physiological data as the adaptive health score. In some examples, the one or more additional adaptive health scores are determined using a different type of first physiological data as the adaptive health score.

In some examples, the assigned first weighted value is increased as the amount of the historic physiological data increases. In some examples, the adaptive health score is a weighted average of the first patient health score and the second patient health score. In some examples, the at least one similar biological, environmental, or behavioral characteristic comprises an age, a gender, a height, a weight, an activity level, a patient demographic, a patient posture, or a combination thereof of each of the patient and the population of patients.

In some examples, the first physiological data comprises heart rate information. In some examples, the first physiological data associated with the patient is continually received at the medical device. In some examples, a frequency of receiving the first physiological data is based at least in part on a type of the first physiological data.

Certain examples of the present disclosure may include some, all, or none of the above advantages or features. One or more other technical advantages or features may be readily apparent to those skilled in the art from the figures, descriptions, and claims included herein. Moreover, while specific advantages or features have been enumerated above, various examples may include all, some, or none of the enumerated advantages or features.

Further scope of the applicability of the described methods and systems will become apparent from the following detailed description, claims, and drawings. The detailed description and specific examples are given by way of illustration only, since various changes and modifications within the spirit and scope of the description will become apparent to those skilled in the art.

DETAILED DESCRIPTION

Figure 1:
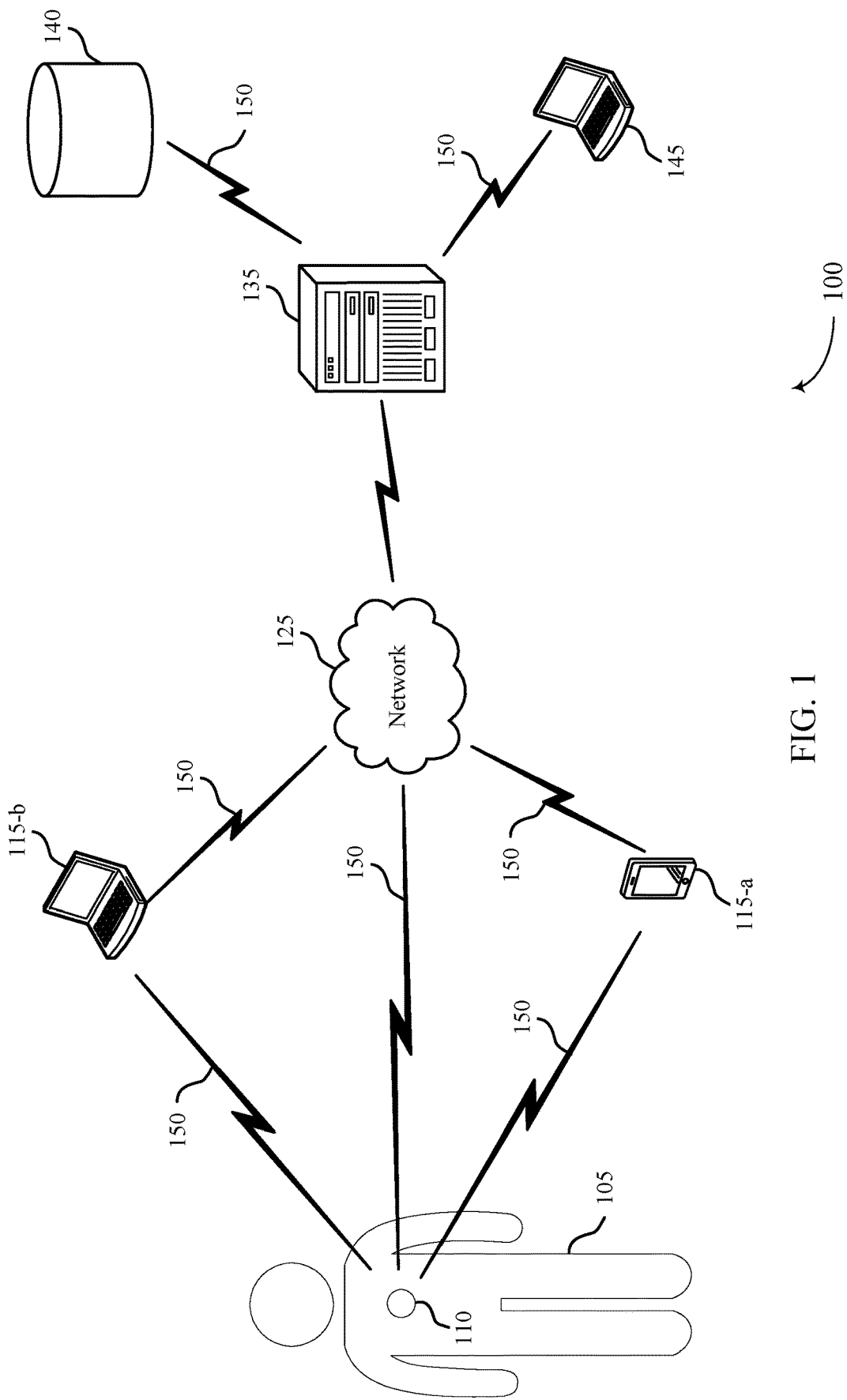
FIG. 1 illustrates an example of a system for determining an adaptive health score associated with a patient in accordance with aspects of the present disclosure.

In a healthcare facility, a variety of monitoring devices may monitor physiological parameters of a patient such as heart rate, blood oxygen saturation levels, respiratory rate, glucose level, etc. A clinical decision support algorithm (e.g., a Modified Early Warning Score (MEWS)) may asses a medical status of a patient, in the form of a score, based on one or more of these physiological parameters. However, such algorithms typically only take into account the patient's current physiological parameters (e.g., the patient's current heart rate). That is, such algorithms do not account for the patient's medical history. Consequently, typical scoring techniques may not provide a comprehensive or accurate assessment of the patient's health. Accordingly, a patient monitoring device capable of assessing one or more physiological parameters of the patient in view of his or her medical history, as well as the medical history of patients sharing one or more similar characteristics, and outputting such an assessment in the form of a score, may result in improved patient monitoring, as well as a more compressive analysis of the patient's health.

In a first example, a medical device may receive first physiological data associated with a patient. The physiological data may include, for example, the patient's heart rate. Upon receiving the physiological data, a first patient health score may be determined. The score may be determined (e.g., calculated) based on a difference between at least one characteristic of the first physiological data and at least one characteristic of historic physiological data associated with the patient. Additionally, for example, a second patient health score may be determined that is based in part on a difference between the at least one characteristic of the first physiological data and at least one characteristic of population physiological data associated with a population of patients. In some examples, each of the patient and the population of patients comprise at least one similar biological, environmental, or behavioral characteristic. A first and second weighted value may be assigned to the first and second patient health scores, respectively. The first weighted value may be assigned as a function of an amount of the historic physiological data and the second weighted value may be assigned as a compliment function of the first weighted value. An adaptive health score for the patient may then be determined based in part on assigning the first and second weighted values.

In an additional example, a medical device may receive first physiological data associated with a patient and subsequently determine a first patient health score. The score may be determined (e.g., calculated) based on a difference between at least one characteristic of the first physiological data and at least one characteristic of historic physiological data associated with the patient. In another example, a second patient health score may be determined that is based in part on a difference between the at least one characteristic of the first physiological data and at least one characteristic of population physiological data associated with a population of patients. A first and second weighted value may be assigned to the first and second patient health scores, respectively. The first weighted value may be assigned as a function of an amount of the historic physiological data and the second weighted value may be assigned as a compliment function of the first weighted value. An adaptive health score for the patient may then be determined based in part on assigning the first and second weighted values. In some examples, the first and second weighted values may be re-assigned based in part on a change in the physiological data. Subsequently, for example, the adaptive health score for the patient may be re-determined based in part on the re-assignment of the first and second weighted values. In another example, the adaptive health score may be aggregated with one or more additional adaptive health scores to form an aggregated adaptive health score. In some examples, the one or more additional adaptive health scores may be determined using a same type of first physiological data as the adaptive health score.

Aspects of the disclosure are initially described in the context of a wireless patient monitoring system. Aspects of the disclosure are further illustrated by and described with reference to apparatus diagrams, system diagrams, and flowcharts that relate to determining an adaptive health score associated with a patient.

FIG. 1 illustrates an example of a patient monitoring system 100 in accordance with various examples of the present disclosure. The patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, or another care facility. The medical device 110 may transmit signals via wired or wireless communications links 150 to computing devices 115 or to a network 125.

The medical device 110 may include one or more sensors configured to collect a variety of physiological parameters (e.g., first physiological data) as well as information related to the location and movement of the patient 105. For example, the medical device 110 may include a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, a sensor which triangulates position from multiple local computing devices 115, or any other sensor configured to collect physiological, location, or motion data associated with the patient 105.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patients nose or mouth). The data collected by the medical device 110 may be transmitted to either the computing devices 115 or to the remote computing device 145 (via the network 125 and central station 135). Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.) Wired data transmissions may occur over Ethernet connections or any other appropriate wired data connection type.

Computing device 115 may be a wireless device such as a tablet, cellular phone, personal digital assistant (PDA), a dedicated receiver, or other similar device or a spatially distributed network of devices configured to receive signals from the medical device 110. In some cases, computing device 115 may be a wireless laptop computer, a clinician Workstation on Wheels, or a smart hospital bed configured to receive signals from the medical device 110. The computing devices 115 may be in communication with a central station 135 via network 125.

The medical device 110 may also communicate directly with the central station 135 via the network 125. The central station 135 may be a server or a central nurse station located within the hospital or in a remote location. The central station 135 may be in further communication with one or more remote computing devices 145, thereby allowing a clinician to remotely monitor the patient 105. The central station 135 may also be in communication with various remote databases 140 where the collected patient data may be stored. In some cases, the remote databases 140 include electronic medical records (EMR) applications for storing and sharing patient data.

In some examples, medical device 110 may receive first physiological data associated with patient 105. As described above, first physiological data may include, for example, data received from a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, or a combination thereof associated with patient 105. In some examples, the medical device 110 may transmit the received physiological data to central station 135 via communication link 150 and network 125.

Upon receiving the first physiological data, the central station 135 may determine a first patient health score of patient 105. In some examples, the first patient health score may include calculating a difference between at least one characteristic of the first physiological data and at least one characteristic of historic physiological data associated with the patient 105. The central station 135 may also determine a second patient health score by calculating a difference between the at least one characteristic of the first physiological data and at least one characteristic of population physiological data associated with a population of patients 105. In some examples, each of the patient 105 and the population of patients 105 may include at least one similar biological, environmental, or behavioral characteristic. The central station may utilize one or more remote databases 140 in calculating the first and second patient health scores. For example, one or more remote databases 140 may include or may store historic physiological data associated with the patient and/or population physiological data associated with a population of patients.

In some examples, the central station 135 may then assign a first weighted value to the first patient health score as a function of an amount of the historic physiological data. In some examples, the central station 135 may then assign a second weighted value to the second patient health score as a compliment function of the first weighted value. The first and second weighted value may, for example, aid in the central station 135 determining the adaptive health score. Stated alternatively, the central station 135 may determine the adaptive health score based at least in part on the assigning of the first and second weighted values. The central station 135 may transmit the adaptive health score—or an indication of the adaptive health score—to one or more remote computing devices 145.

Figure 2:
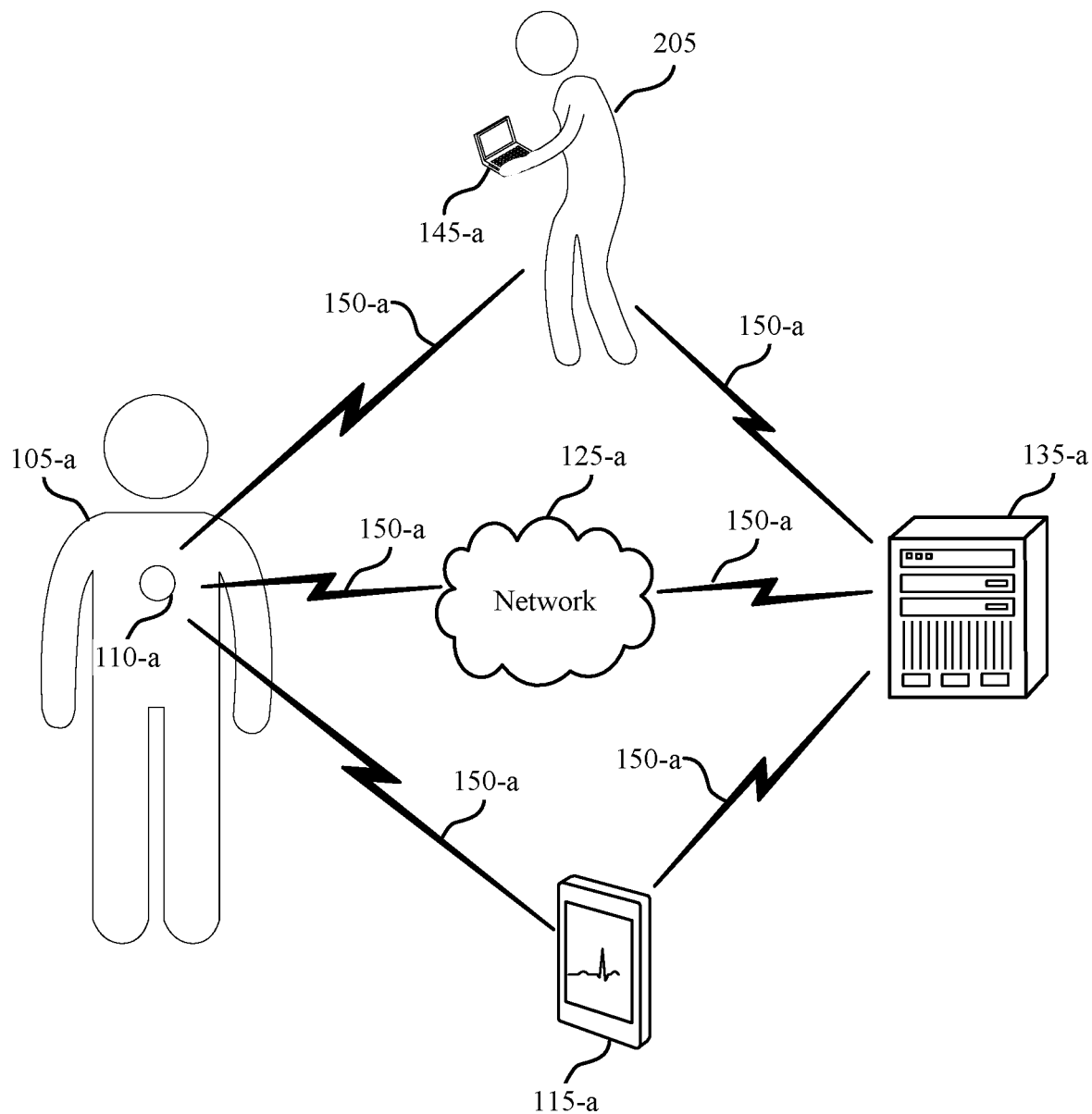
FIG. 2 illustrates an example system for determining an adaptive health score associated with a patient in accordance with aspects of the present disclosure.

FIG. 2 illustrates an example of a patient monitoring system 200 that supports determining an adaptive health score associated with a patient. The patient monitoring system 200 may be an example of aspects of patient monitoring system 100 and may include a patient 105-a wearing, carrying, or otherwise coupled with a medical device 110-a. The medical device 110-a may be an example of medical device 110 as described with reference to FIG. 1, and may include one or more sensors configured to measure a variety of physiological parameters associated with the patient 105-a. Medical device 110-a may also aid in the determination of an adaptive health score associated with the patient 105-a. In some examples, the patient monitoring system 200 may also include a clinician 205; a computing device 115-a, which may be an example of computing device 115 as described with reference to FIG. 1; a remote computing device 145-a, which may be an example of remote computing device 145 as described with reference to FIG. 1; a network 125-a, which may be an example of network 125 as described with reference to FIG. 1; and a central station 135-a, which may be an example of central station 135-a as described with reference to FIG. 1. Each of the components illustrated may be connected via communication links 150-a, which may be examples of communication links 150 as described with reference to FIG. 1.

In some examples, medical device 110-a may receive first physiological data associated with the patient 105-a. The data may be received, for example, continuously from the patient 105-a, or at one or more specific times. In some examples, the first physiological data may include heart rate information of the patient 105-a. In other examples, the first physiological data may include data received from a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, or a combination thereof associated with the patient 105-a. Additionally, as described above, the medical device 110-a may be directly coupled with the patient 105-a to receive the first physiological data.

The medical device 110-a may transmit the first physiological data to, for example, central station 135-a. In some examples, the medical device 110-a may transmit the first physiological data to central station 135-a through the network 125-a (e.g., wirelessly via communication link 150-a). Transmitting the first physiological data to the central station 135-a may, for example, aid in the determination of an adaptive health score. In other examples, the medical device 110-a may transmit the first physiological data directly to computing device 115-a through the network 125-a (e.g., wirelessly via communication link 150-a). The computing device 115-a may receive the first physiological data and, in some examples, may display the data instantaneously (e.g., display the heart rate of patient 105-a).

As described above, in some examples, the medical device 110-a may transmit the first physiological data to central station 135-a through the network 125-a. The central station 135-a may receive the first physiological data and determine a first patient health score. In some examples, the first patient health score may be determined based on calculating a difference between at least one characteristic of the first physiological data and at least one characteristic of historic physiological data associated with the patient. For example, the medical device 110-a may be monitoring the heart rate of patient 105-a. Thus, upon receiving the data associated with the heart rate of the patient 105-a, the central station 135-a may compare the received heart rate data with historical heart rate data of patient 105-a. In some examples, the comparison may be based on at least one characteristic of the data. Meaning that, in some examples, a same or similar data point or a same or similar set of the received data may be compared with historical data associated with the patient 105-a. For example, the received physiological data may be compared with the historical physiological data over a same time-period (e.g., comparing heart rate data over a same time interval). In some examples, the historical heart rate data of patient 105-a may be stored at and received from a database (e.g., remote database 140 as described with reference to FIG. 1) in communication with the central station 135-a.

In some examples, the central station 135-a may determine a second patient health score associated with the received first physiological data. For example, the central station 135-a may determine the second patient health score based on calculating a difference between the at least one characteristic of the first physiological data and at least one characteristic of population physiological data associated with a population of patients. In some examples, each of the patient and the population of patients include at least one similar biological, environmental, or behavioral characteristic. For example, as described above, the medical device 110-a may be monitoring the heart rate of patient 105-a. Thus, upon receiving the data associated with the heart rate of the patient 105-a, the central station 135-a may compare the received heart rate data with historical heart rate data of a population of patients. In some examples, the comparison may be based on patient 105-a and the population of patients sharing at least one similar biological, environmental, or behavioral characteristic. The similar biological, environmental, or behavioral characteristic may include, for example, a similar age, gender, height, weight, activity level, patient demographic, patient posture, or a combination thereof. Thus the received physiological data may be compared with the population physiological data in the instance that some similarity exists between patient 105-a and the patient or patients to which the physiological data is being compared. This may lead to a more accurate score prediction, as patients that share similar biological, environmental, or behavioral characteristics may experience the same or similar health-related attributes. In some examples, the patient population data may be stored at and receive from a database (e.g., remote database 140 as described with reference to FIG. 1) in communication with the central station 135-a.

Upon determining the first and second patient health scores, the central station 135-a may assign a first weighted value to the first patient health score as a function of an amount of the historic physiological data. Stated alternatively, the first weighted value may be assigned based on an amount of historic physiological data available or an amount of historic physiological data used in the determination of the first patient health score. In some examples, the first weighted value may increase as the amount of historic physiological data increases. For example, of more historical data was used or was available to be used, the weighted value might differ than if less historical data was used or was available to be used. In some examples, upon assigning the first weighted value, the central station 135-a may assign a second weighted value to the second patient health score as a compliment function of the first weighted value. Meaning that, in some examples, the sum of the first patient health score and the second patient health score may not exceed a value of "1." Thus, in some examples, assigning the second weighted value to the second patient health score may be described as an inverse function of the first weighted value. In either example, the central station 135-a may determine the adaptive health score based at least in part on the assigning of the first and second weighted values. For example, the adaptive health score may be an average of the first patient health score and the second patient health score. In some examples, the central station 135-a may transmit—via network 125-a—the adaptive health score to, for example, a remote computing device 145-a such that the score may be viewed and/or monitored by a clinician 205.

Additionally or alternatively, for example, the central station 135-a may re-assign the first weighted value and the second weighted value to each of the first patient health score and the second patient health score based at least in part on a change in the first physiological data. In some examples, the change may be based on the medical device 110-a receiving additional physiological data (e.g., additional heart rate data). In other examples, the change may be based on the medical device 110-a receiving different physiological data (e.g., receiving blood pressure data instead of heart rate data). In some examples, the central station 135-a may re-determine the adaptive health score based at least in part on the re-assignment of the first weighted value and the second weighted value. Thus, in some examples, to re-determine the adaptive health score, the central station 135-a may also re-determine the first and second patient health scores based in part on the change in physiological data.

In some examples, the central station 135-a may receive the first physiological data associated with the patient 105-a at a first time and may also receive the first physiological data associated with the patient at a second time different from the first time. In some examples, the re-assignment of the weighted value to the first patient health score and the second patient health score may be based at least in part on a change in the first physiological data from the first time to the second time. A mechanism such as a timer may be activated to determine that a predetermined time interval has been exceeded. For example, the adaptive health score of patient 105-a may be determined at predetermined intervals (e.g., every ten minutes). Thus, the adaptive health score of patient 105-a may be calculated and a timer may begin.

After a predetermined amount of time, the first physiological data of patent 105-a may be re-received (e.g., by medical device 110-a) and transmitted to central station 135-a. After the transmission, the central station 135-a may recalculate the first and second patient health scores and, in some examples, re-assign the first and second weighted values. Thus, the central station 135-a may ultimately re-determine the adaptive health score based in part on a change in the physiological data from the first time to the second time.

Additionally or alternatively, for example, the medical device 110-a may receive second physiological data associated with the patient 105-a that is different from the first physiological data. In some examples, the determination of the first patient health score and the second patient health score may be based at least in part on the second physiological data received. Stated alternatively, the medical device 110-a may receive different physiological information and determine the first and second patient health scores based on the different physiological data. For example, as described above, medical device 110-a may receive heart rate information of patient 105-a. However, it may be desirable to determine an adaptive health score of patient 105-a based on, for example, the patient's blood pressure. Thus, the medical device 110-a may receive blood pressure data (e.g., second physiological information) of patient 105-a. The central station 135-a may ultimately receive this data, determine a first and second patient health score based on the data, assign first and second weighted value to the patient health scores, and determine the adaptive health score based on the new (e.g., second) physiological data.

In other examples, the central station 135-a may aggregate the adaptive health score with one or more additional adaptive health scores to form an aggregated adaptive health score. In some examples, the one or more additional adaptive health scores may be determined using a same type of first physiological data as the adaptive health score. For example, the central station 135-a may, upon determining an adaptive health score, store the adaptive health score associated with patient 105-a to a database. In some examples, the central station 135-a may utilize the stored adaptive health score in a subsequent determination of an updated adaptive health score for the patient 105-a. For example, when determining an adaptive health score for a same type of physiological data (e.g., heart rate data), the central station 135-a reference the stored score in its determination. In some examples, the central station 135-a may average each of the stored adaptive health scores with its current calculation to determine an adaptive health score for patient 105-a.

Figure 3:
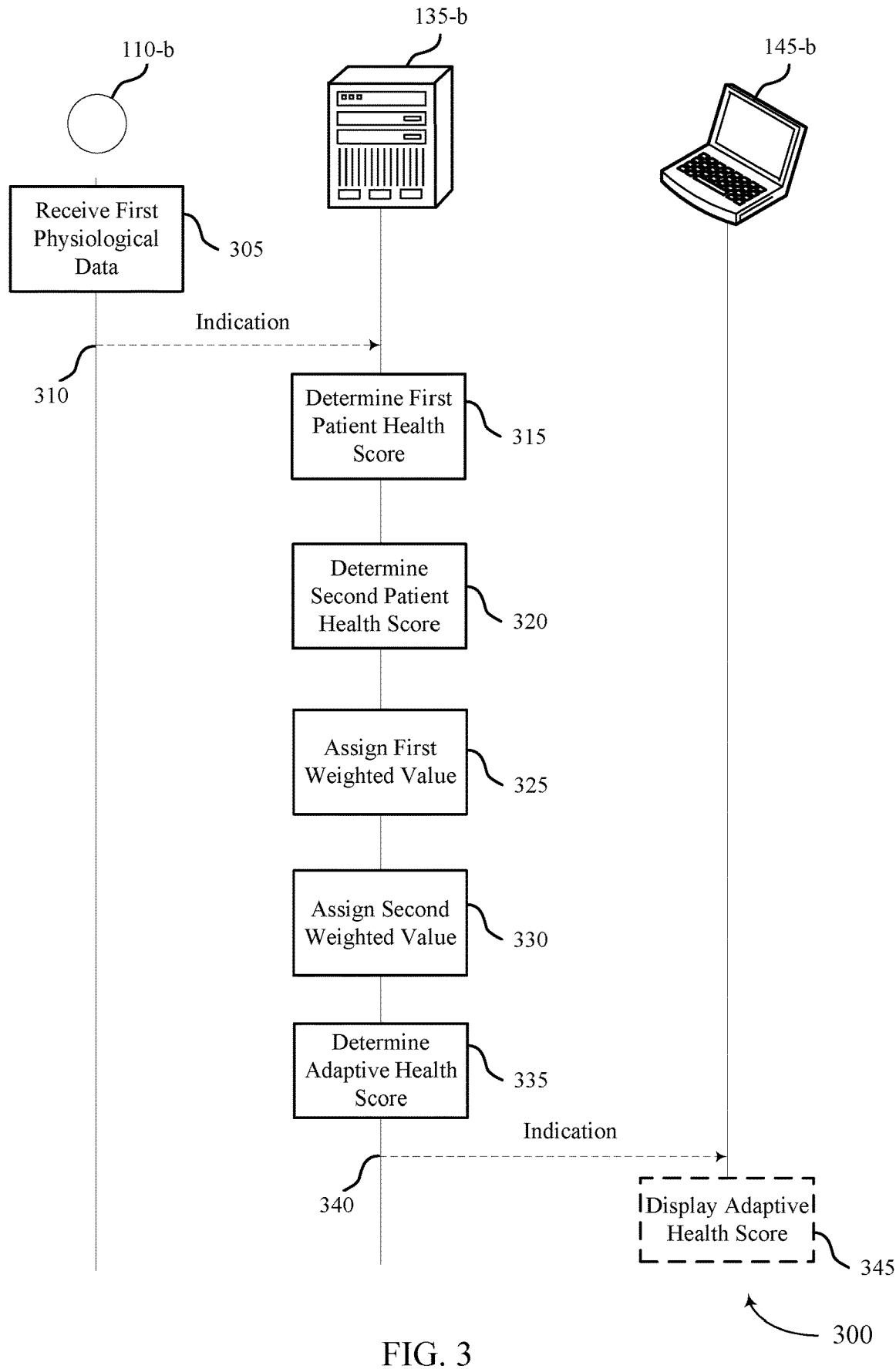
FIG. 3 illustrates a flow diagram for determining an adaptive health score associated with a patient in accordance with aspects of the present disclosure.

FIG. 3 illustrates an example process flow 300 that supports determining an adaptive health score associated with a patient. Process flow 300 may include medical device 110-b, central station 135-b, and remote computing device 145-b, which may be respective examples of a medical device, central station 135, and remote computing device 145 as described in reference to FIGS. 1 and 2. Alternative examples of the following may be implemented, where some steps are performed in a different order or not at all. Some steps may additionally include additional features not mentioned above.

Medical device 110-b may receive first physiological data associated with a patient (e.g., patient 105-a as described with reference to FIG. 2). As described above, first physiological data may include heart rate information of the patient or, in other examples, may include data received from a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, or a combination thereof. Upon receiving the first physiological data, medical device 110-b may transmit 310 the received data—or an indication of the received data—to central station 135-b.

At block 315, central station 135-b may determine a first patient health score. In some examples, the first patient health score determination may include calculating a difference between at least one characteristic of the first physiological data and at least one characteristic of historic physiological data associated with the patient. Central station 135-b may determine the first patient health score based on receiving the first physiological data or the indication of the first physiological data. In other examples, the central station 135-b may re-determine the first patient health score based on receiving second physiological data associated with the patient, or updated physiological data associated with the patient.

At block 320, central station 135-b may determine a second patient health score. In some examples, the second patient health score determination may include calculating a difference between the at least one characteristic of the first physiological data and at least one characteristic of population physiological data associated with a population of patients. In some examples, each of the patient and the population of patients may include at least one similar biological, environmental, or behavioral characteristic. Central station 135-b may determine the second patient health score based on calculating the first patient health score. In other examples, the central station 135-b may re-determine the second patient health score based on receiving second physiological data associated with the patient, or updated physiological data associated with the patient.

At block 325, central station 135-b may assign a first weighted value to the first patient health score as a function of an amount of the historic physiological data. In some examples, the central station 135-b may re-assign the first weighted value to the first patient health score based at least in part on a change in the first physiological data. In other examples, the central station 135-b may increase the assigned first weighted value as the amount of historic physiological data increases.

At block 330, central station central station 135-b may assign a second weighted value to the second patient health score as a compliment function of the first weighted value. In some examples, the compliment function may be referred to as an inverse function. In other examples, the central station 135-b may re-assign the second weighted value to the second patient health score based at least in part on a change in the first physiological data.

At block 335, central station 135-b may determine the adaptive health score based at least in part on the assigning of the first and second weighted values. In other examples, the central station 135-b may re-determine the adaptive health score based at least in part on the re-assignment of the first weighted value and the second weighted value, as described above. In some examples, the central station 135-b may transmit the adaptive health score—or an indication of the adaptive health score—based on the determination. For example, the central station 135-b may transmit an indication of the adaptive health score to remote computing device 145-b and the adaptive health score may be displayed, in some examples, at block 345. The adaptive health score may be displayed such that a clinician (e.g., clinician 205 as described with reference to FIG. 2) may review and/or monitor the score.

By way of example, a medical device may receive first physiological data associated with a patient. The physiological data may be heart rate information of the patient. For example, when the heart rate data is received, the patient's heart rate may be 104 beats per minute (BPM). In some examples, a first patient health score may be determined based on receiving the heart rate information. The first patient health score, as described above, may be a calculation of a difference between at least one characteristic of the physiological data and at least one characteristic of historic physiological data associated with the patient. In some examples, one additional measurement of the patient's heart rate may have been taken, which may have been 105 BPM. Thus, the first patient health score may be calculated as a difference between the patient data (e.g., 104 BPM) and the historical data of the patient (e.g., 105 BPM due to the existence of little historical data). Thus, in such an example, the first patient health score may be 1.

In some examples, a second patient health score may be determined. The second patient health score may include calculating a difference between the at least one characteristic of the first physiological data and at least one characteristic of population physiological data associated with a population of patients. In some examples, each of the patient and the population of patients comprise at least one similar biological, environmental, or behavioral characteristic. For example, the at least one similar characteristic may be a same age. Thus the patient's heart rate information may be compared with the heart rate information of a same-age patient for use in calculation of the second patient health score. For example, the heart rate information of the same-age patient may be 85 BPM. Thus, the second health score may be a difference between 104 BPM and 85 BPM, or 19.

In another example, a first weighted value may be assigned to the first patient health score as a function of an amount of historical physiological data. Because little historic patient physiological data existed at the time of calculating the first patient health score, the weighted value may be 0.1. In some examples, a second weighted value may be assigned to the second patient health score as a compliment function of the first weighted value. Because the first weighted value was 0.1, and because the second weighted value is assigned as a compliment function, the second weighted value may be 0.9 (e.g., 0.1+0.9=1.0). In some examples, the adaptive health score of the patient may be determined based at least in part on assigning the first and second weighted values. For example, the calculation of the adaptive health score may begin with multiplying the first patient health score by the first weighted value and multiplying the second patient health score by the second weighted value. These two scores may then be added together (e.g., (1×0.1)+(19×0.9)). This value may then be divided by a sum of the first patient health score and the second patient health score (e.g., ((1×0.1)+(19×0.9))/(1+19)). The resulting value may then be multiplied by 100 (e.g., 0.86×100=86) to calculate the patient health score. Thus, in such an example, the patient health is approximately 86.

In a further example, the patient's heart rate may be 98 BPM. The first patient health score, as described above, may be a calculation of a difference between at least one characteristic of the physiological data and at least one characteristic of historic physiological data associated with the patient. Because the received heart rate information as received at a subsequent time as compared with the calculation above, historical patient health data may exist. For example, the historical patient heart rate data may be an average of each of the previous heart rate measurements. By way of example, the historical patient heart rate data may be 100.6364 BPM. Thus, the first patient health score may be calculated as a difference between the patient data (e.g., 98 BPM) and the historical data of the patient (e.g., 100.6364 BPM). Thus, in such an example, the first patient health score may be 2.6364.

In some examples, a second patient health score may be determined. The second patient health score may include calculating a difference between the at least one characteristic of the first physiological data and at least one characteristic of population physiological data associated with a population of patients. In some examples, each of the patient and the population of patients comprise at least one similar biological, environmental, or behavioral characteristic. For example, the at least one similar characteristic may be a same age. Thus the patient's heart rate information may be compared with the heart rate information of a same-age patient for use in calculation of the second patient health score. For example, the heart rate information of the same image patient may be 85 BPM. Thus, the second health score may be a difference between 98 BPM and 85 BPM, or 13.

As described above, a first weighted value may be assigned to the first patient health score as a function of an amount of historical physiological data. Based on the amount of historical heart rate data collected (e.g., to average 100.6364 BPM), the weighted average may be 0.2. In some examples, a second weighted value may be assigned to the second patient health score as a compliment function of the first weighted value. Because the first weighted value was 0.2, and because the second weighted value is assigned as a compliment function, the second weighted value may be 0.8 (e.g., 0.2+0.8=1.0). In some examples, the adaptive health score of the patient may be determined based at least in part on assigning the first and second weighted values. For example, the calculation of the adaptive health score may begin with multiplying the first patient health score by the first weighted value and multiplying the second patient health score by the second weighted value. These two scores may then be added together (e.g., (2.6364×0.2)+(13×0.8)). This value may then be divided by a sum of the first patient health score and the second patient health score (e.g., ((2.6364×0.2)+(13×0.8))/(2.6364+13)). The resulting value may then be multiplied by 100 (e.g., 0.7×100=70) to calculate the patient health score. Thus, in such an example, the patient health is approximately 70. In some examples, when compared with the prior adaptive health score of 86, an adaptive health score of 70 may indicate an improvement in the patient's overall health.

In a final example, the patient's heart rate may be 85 BPM. The first patient health score, as described above, may be a calculation of a difference between at least one characteristic of the physiological data and at least one characteristic of historic physiological data associated with the patient. Because the received heart rate information as received at a subsequent time as compared with the calculation above, additional historical patient health data may exist. For example, the historical patient heart rate data may be an average of each of the previous heart rate measurements. By way of example, the historical patient heart rate data may be 98.4 BPM. Thus, the first patient health score may be calculated as a difference between the patient data (e.g., 85 BPM) and the historical data of the patient (e.g., 98.4 BPM). Thus, in such an example, the first patient health score may be 13.4.

In some examples, a second patient health score may be determined. The second patient health score may include calculating a difference between the at least one characteristic of the first physiological data and at least one characteristic of population physiological data associated with a population of patients. In some examples, each of the patient and the population of patients comprise at least one similar biological, environmental, or behavioral characteristic. For example, the at least one similar characteristic may be a same age. Thus the patient's heart rate information may be compared with the heart rate information of a same-age patient for use in calculation of the second patient health score. For example, the heart rate information of the same-age patient may be 85 BPM. Thus, the second health score may be a difference between 85 BPM and 85 BPM, or 0.

As described above, a first weighted value may be assigned to the first patient health score as a function of an amount of historical physiological data. Based on the amount of historical heart rate data collected (e.g., to average 98.4 BPM), the weighted average may be 0.4. In some examples, a second weighted value may be assigned to the second patient health score as a compliment function of the first weighted value. Because the first weighted value was 0.4, and because the second weighted value is assigned as a compliment function, the second weighted value may be 0.6 (e.g., 0.4±0.6=1.0), In some examples, the adaptive health score of the patient may be determined based at least in part on assigning the first and second weighted values. For example, the calculation of the adaptive health score may begin with multiplying the first patient health score by the first weighted value and multiplying the second patient health score by the second weighted value. These two scores may then be added together (e.g., (13.4×0.4)+(0×0.6)). This value may then be divided by a sum of the first patient health score and the second patient health score (e.g., ((13.4×0.4)+(0×0.6))/(13.4+0)). The resulting value may then be multiplied by 100 (e.g., 0.4×100=40) to calculate the patient health score. Thus, in such an example, the patient health is approximately 40. In some examples, when compared with the prior adaptive health score of 70, an adaptive health score of 40 may indicate an improvement in the patient's overall health.

Figure 4:
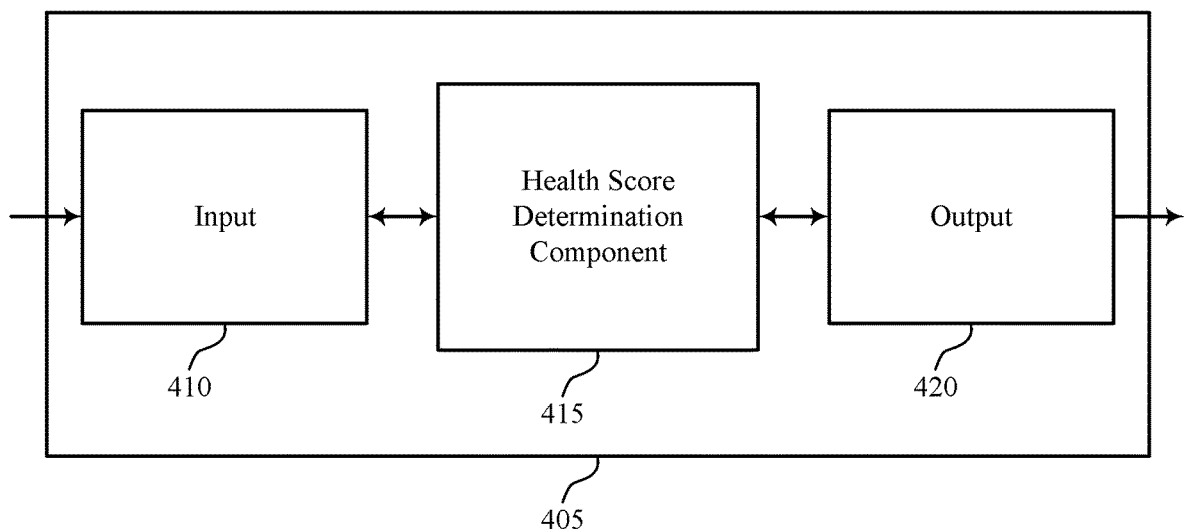
FIGS. 4 through 6 show block diagrams of a device that supports adaptive health score in accordance with aspects of the present disclosure.

FIG. 4 shows a block diagram 400 of a device 405 that supports adaptive health score in accordance with aspects of the present disclosure. Device 405 may be an example of aspects of a medical device (e.g., medical device 110 as described with reference to FIG. 1) as described herein. Device 405 may include input 410, health score determination component 415, and output 420. Device 405 may also include a processor. Each of these components may be in communication with one another (e.g., via one or more buses).

Health score determination component 415 may be an example of aspects of the health score determination component 715 described with reference to FIG. 7.

Health score determination component 415 and/or at least some of its various sub-components may be implemented in hardware, software executed by a processor, firmware, or any combination thereof. If implemented in software executed by a processor, the functions of the health score determination component 415 and/or at least some of its various sub-components may be executed by a general-purpose processor, a digital signal processor (DSP), an application-specific integrated circuit (ASIC), an field-programmable gate army (FPGA) or other programmable logic device, discrete gate or transistor logic, discrete hardware components, or any combination thereof designed to perform the functions described in the present disclosure. The health score determination component 415 and/or at least some of its various sub-components may be physically located at various positions, including being distributed such that portions of functions are implemented at different physical locations by one or more physical devices. In some examples, health score determination component 415 and/or at least some of its various sub-components may be a separate and distinct component in accordance with various aspects of the present disclosure. In other examples, health score determination component 415 and/or at least some of its various sub-components may be combined with one or more other hardware components, including but not limited to an I/O component, a transceiver, a network server, another computing device, one or more other components described in the present disclosure, or a combination thereof in accordance with various aspects of the present disclosure.

Health score determination component 415 may receive, at a medical device, first physiological data associated with the patient, determine a first patient health score, the first patient health score determination including calculating a difference between at least one characteristic of the first physiological data and at least one characteristic of historic physiological data associated with the patient, determine a second patient health score, the second patient health score determination including calculating a difference between the at least one characteristic of the first physiological data and at least one characteristic of population physiological data associated with a population of patients, where each of the patient and the population of patients include at least one similar biological, environmental, or behavioral characteristic, assign a first weighted value to the first patient health score as a function of an amount of the historic physiological data, assign a second weighted value to the second patient health score as an compliment function of the first weighted value, and determine the adaptive health score based on the assigning of the first and second weighted values.

Figure 5:
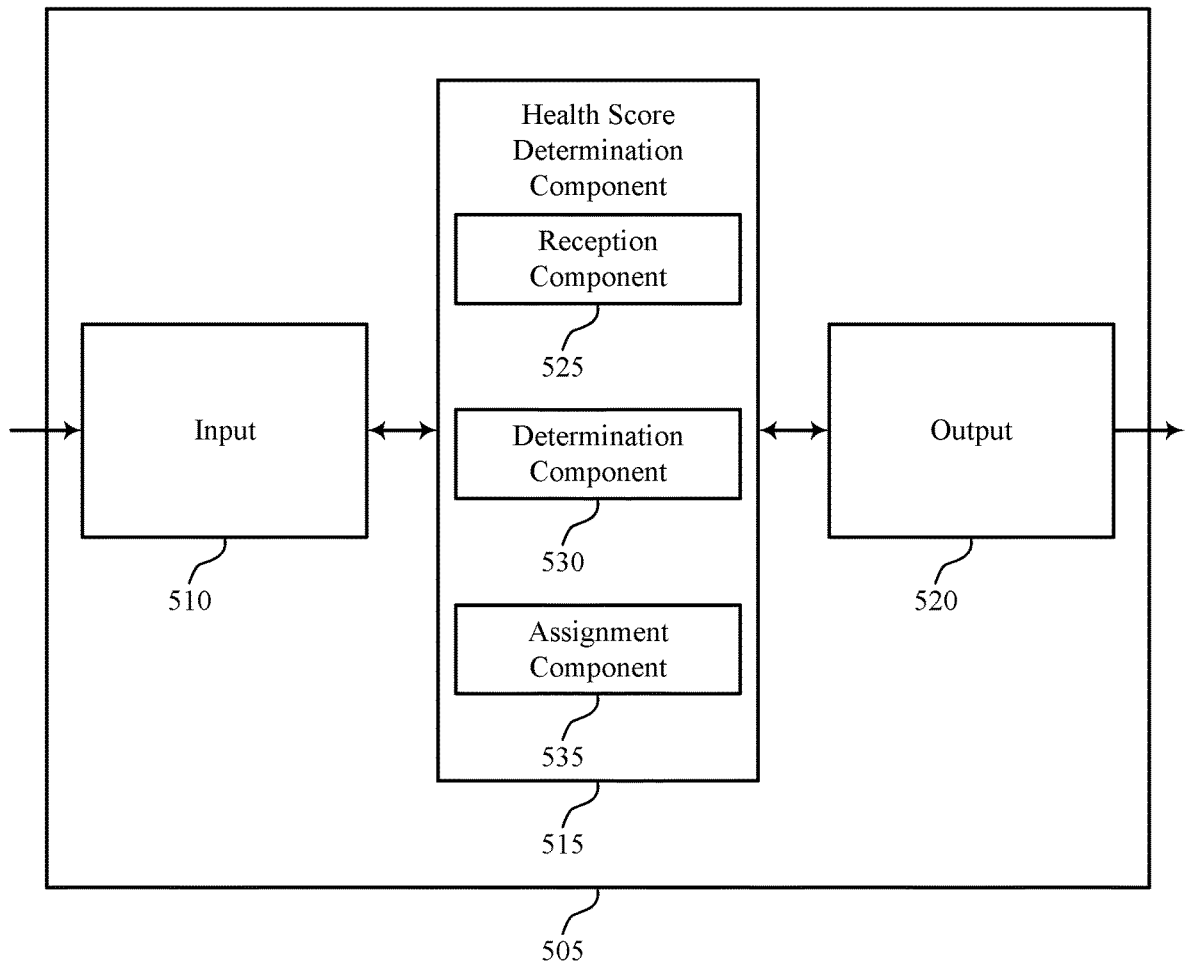

FIG. 5 shows a block diagram 500 of a device 505 that supports adaptive health score in accordance with aspects of the present disclosure. Device 505 may be an example of aspects of a device 405 as described with reference to FIG. 4, or a medical device (e.g., medical device 110 as described with reference to FIG. 1) as described herein. Device 505 may include input 510, health score determination component 515, and output 520. Device 505 may also include a processor. Each of these components may be in communication with one another (e.g., via one or more buses).

Health score determination component 515 may be an example of aspects of the health score determination component 715 described with reference to FIG. 7. Health score determination component 515 may also include reception component 525, determination component 530, and assignment component 535.

Reception component 525 may receive, at a medical device, first physiological data associated with the patient. In other examples, reception component 525 may receive the first physiological data associated with the patient at a first time. In another example, reception component 525 may receive the first physiological data associated with the patient at a second time different from the first time, where the re-assignment of the weighted value to the first patient health score and the second patient health score is based on a change in the first physiological data from the first time to the second time. In other examples, reception component 525 may receive, at the medical device, second physiological data associated with the patient that is different from the first physiological data, where the determination of the first patient health score and the second patient health score are based on the second physiological data received. In some cases, the first physiological data associated with the patient may be continually received at the medical device. In some cases, a frequency of receiving the first physiological data may be based on a type of the first physiological data.

Determination component 530 may determine a first patient health score, the first patient health score determination including calculating a difference between at least one characteristic of the first physiological data and at least one characteristic of historic physiological data associated with the patient. In other examples, determination component 530 may determine a second patient health score, the second patient health score determination including calculating a difference between the at least one characteristic of the first physiological data and at least one characteristic of population physiological data associated with a population of patients, where each of the patient and the population of patients include at least one similar biological, environmental, or behavioral characteristic. In other examples, determination component 530 may determine the adaptive health score based on the assigning of the first and second weighted values, and re-determine the adaptive health score based on the re-assignment of the first weighted value and the second weighted value. In some cases, the at least one similar biological, environmental, or behavioral characteristic may include an age, a gender, a height, a weight, an activity level, a patient demographic, a patient posture, or a combination thereof of each of the patient and the population of patients. In some cases, the first physiological data may include heart rate information.

Assignment component 535 may assign a first weighted value to the first patient health score as a function of an amount of the historic physiological data. In other examples, assignment component 535 may assign a second weighted value to the second patient health score as an compliment function of the first weighted value. In some examples, assignment component 535 may re-assign the first weighted value and the second weighted value to each of the first patient health score and the second patient health score based on a change in the first physiological data. In some cases, the assigned first weighted value may be increased as the amount of the historic physiological data increases. In some cases, the adaptive health score may be a weighted average of the first patient health score and the second patient health score.

Figure 6:
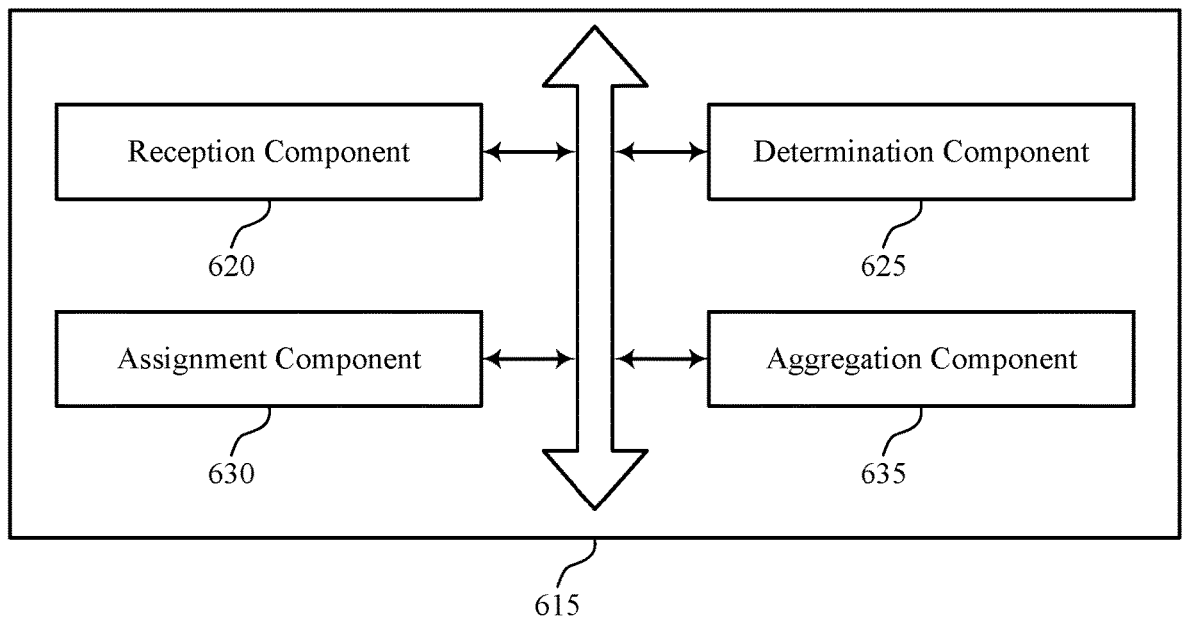

FIG. 6 shows a block diagram 600 of a health score determination component 615 that supports adaptive health score in accordance with aspects of the present disclosure. The health score determination component 615 may be an example of aspects of a health score determination component 415, a health score determination component 515, or a health score determination component 715 described with reference to FIGS. 4, 5, and 7. The health score determination component 615 may include reception component 620, determination component 625, assignment component 630, and aggregation component 635, Each of these modules may communicate, directly or indirectly, with one another (e.g., via one or more buses).

Reception component 620 may receive, at a medical device, first physiological data associated with the patient. In some examples, reception component 620 may receive the first physiological data associated with the patient at a first time. In other examples, reception component 620 may receive the first physiological data associated with the patient at a second time different from the first time, where the re-assignment of the weighted value to the first patient health score and the second patient health score is based on a change in the first physiological data from the first time to the second time. In some examples, reception component 620 may receive, at the medical device, second physiological data associated with the patient that is different from the first physiological data, where the determination of the first patient health score and the second patient health score are based on the second physiological data received. In some cases, the first physiological data associated with the patient may be continually received at the medical device. In some cases, a frequency of receiving the first physiological data may be based on a type of the first physiological data.

Determination component 625 may determine a first patient health score, the first patient health score determination including calculating a difference between at least one characteristic of the first physiological data and at least one characteristic of historic physiological data associated with the patient. In other examples, determination component 625 may determine a second patient health score, the second patient health score determination including calculating a difference between the at least one characteristic of the first physiological data and at least one characteristic of population physiological data associated with a population of patients, where each of the patient and the population of patients include at least one similar biological, environmental, or behavioral characteristic. In some examples, determination component 625 may determine the adaptive health score based on the assigning of the first and second weighted values. In other examples, determination component 625 may re-determine the adaptive health score based on the re-assignment of the first weighted value and the second weighted value. In some cases, the at least one similar biological, environmental, or behavioral characteristic may include an age, a gender, a height, a weight, an activity level, a patient demographic, a patient posture, or a combination thereof of each of the patient and the population of patients. In some cases, the first physiological data may include heart rate information.

Assignment component 630 may assign a first weighted value to the first patient health score as a function of an amount of the historic physiological data. In other examples, assignment component 630 may assign a second weighted value to the second patient health score as an compliment function of the first weighted value. In some examples, assignment component 630 may re-assign the first weighted value and the second weighted value to each of the first patient health score and the second patient health score based on a change in the first physiological data. In some cases, the assigned first weighted value may be increased as the amount of the historic physiological data increases. In some cases, the adaptive health score may be a weighted average of the first patient health score and the second patient health score.

Aggregation component 635 may aggregate the adaptive health score with one or more additional adaptive health scores to form an aggregated adaptive health score, where the one or more additional adaptive health scores are determined using a same type of first physiological data as the adaptive health score. In some cases, the one or more additional adaptive health scores may be determined using a different type of first physiological data as the adaptive health score.

Figure 7:
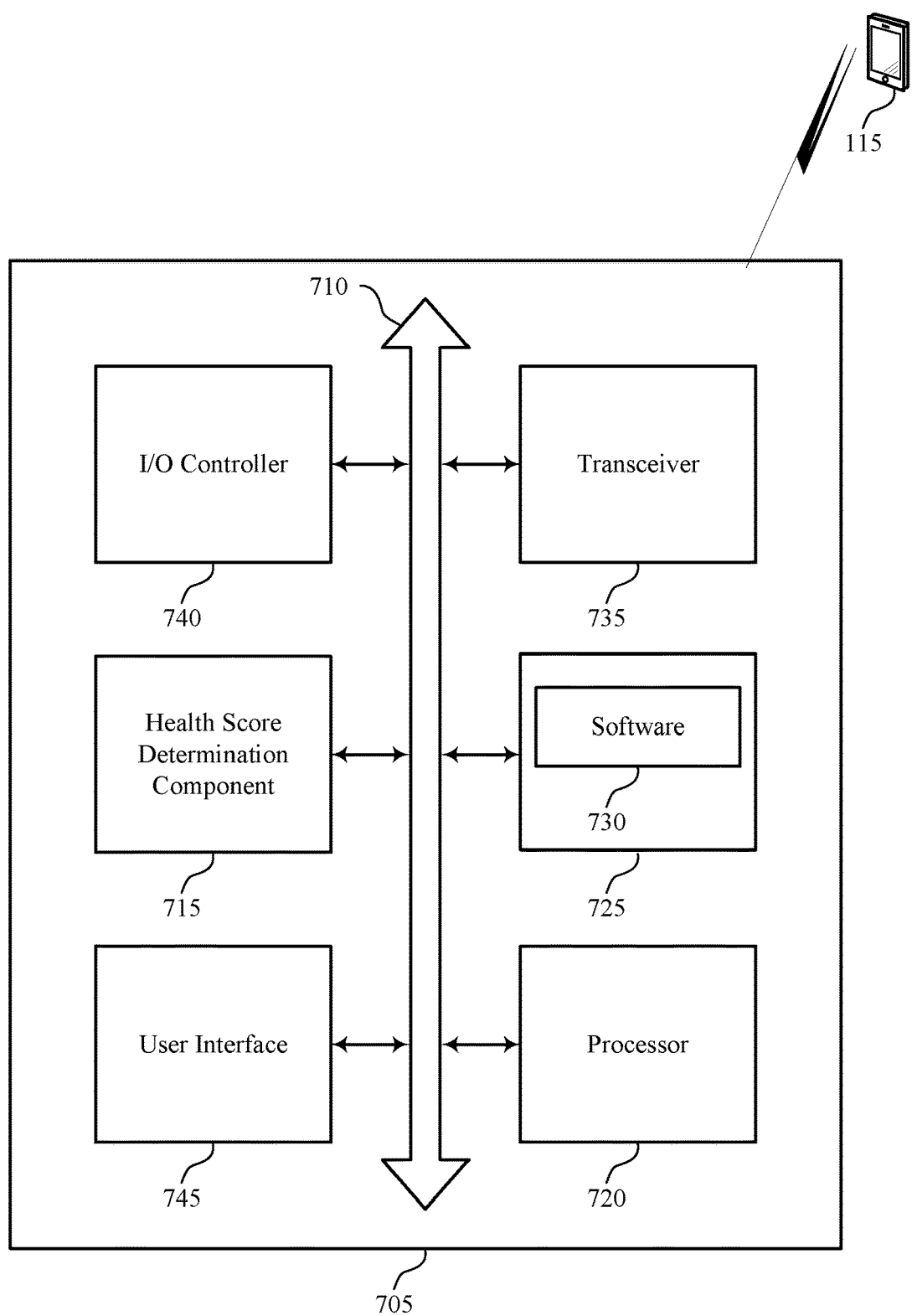
FIG. 7 illustrates a block diagram of a system including a medical device that supports adaptive health score in accordance with aspects of the present disclosure.

FIG. 7 shows a diagram of a system 700 including a device 705 that supports adaptive health score in accordance with aspects of the present disclosure. Device 705 may be an example of or include the components of device 405, device 505, or a medical device (e.g., medical device 110 as described with reference to FIG. 1) as described above, e.g., with reference to FIGS. 1, 4, and 5. Device 705 may include components for bi-directional voice and data communications including components for transmitting and receiving communications, including health score determination component 715, processor 720, memory 725, software 730, transceiver 735, I/O controller 740, and user interface 745. These components may be in electronic communication via one or more buses (e.g., bus 710).

Processor 720 may include an intelligent hardware device, (e.g., a general-purpose processor, a DSP, a central processing unit (CPU), a microcontroller, an ASIC, an FPGA, a programmable logic device, a discrete gate or transistor logic component, a discrete hardware component, or any combination thereof). In some cases, processor 720 may be configured to operate a memory array using a memory controller. In other cases, a memory controller may be integrated into processor 720. Processor 720 may be configured to execute computer-readable instructions stored in a memory to perform various functions (e.g., functions or tasks supporting adaptive health score).

Memory 725 may include random access memory (RAM) and read only memory (ROM). The memory 725 may store computer-readable, computer-executable software 730 including instructions that, when executed, cause the processor to perform various functions described herein. In some cases, the memory 725 may contain, among other things, a basic input/output system (BIOS) which may control basic hardware or software operation such as the interaction with peripheral components or devices.

Software 730 may include code to implement aspects of the present disclosure, including code to support adaptive health score. Software 730 may be stored in a non-transitory computer-readable medium such as system memory or other memory. In some cases, the software 730 may not be directly executable by the processor but may cause a computer (e.g., when compiled and executed) to perform functions described herein.

Transceiver 735 may communicate bi-directionally, via one or more antennas, wired, or wireless links as described above. For example, the transceiver 735 may represent a wireless transceiver and may communicate bi-directionally with another wireless transceiver. The transceiver 735 may also include a modem to modulate the packets and provide the modulated packets to the antennas for transmission, and to demodulate packets received from the antennas.

I/O controller 740 may manage input and output signals for device 705. I/O controller 740 may also manage peripherals not integrated into device 705. In some cases, I/O controller 740 may represent a physical connection or port to an external peripheral. In some cases, I/O controller 740 may utilize an operating system such as iOS®, ANDROID®, MS-DOS®, MS-WINDOWS®, OS/2®, UNIX®, LIMA®, or another known operating system. In other cases, I/O controller 740 may represent or interact with a modem, a keyboard, a mouse, a touchscreen, or a similar device. In some cases, I/O controller 740 may be implemented as part of a processor. In some cases, a user may interact with device 705 via I/O controller 740 or via hardware components controlled by I/O controller 740.

User interface 745 may enable a user to interact with device 705. In some examples, the user interface 745 may include an audio device, such as an external speaker system, an external display device such as a display screen, or an input device (e.g., remote control device interfaced with the user interface 745 directly or through the I/O controller module).

Figure 8:
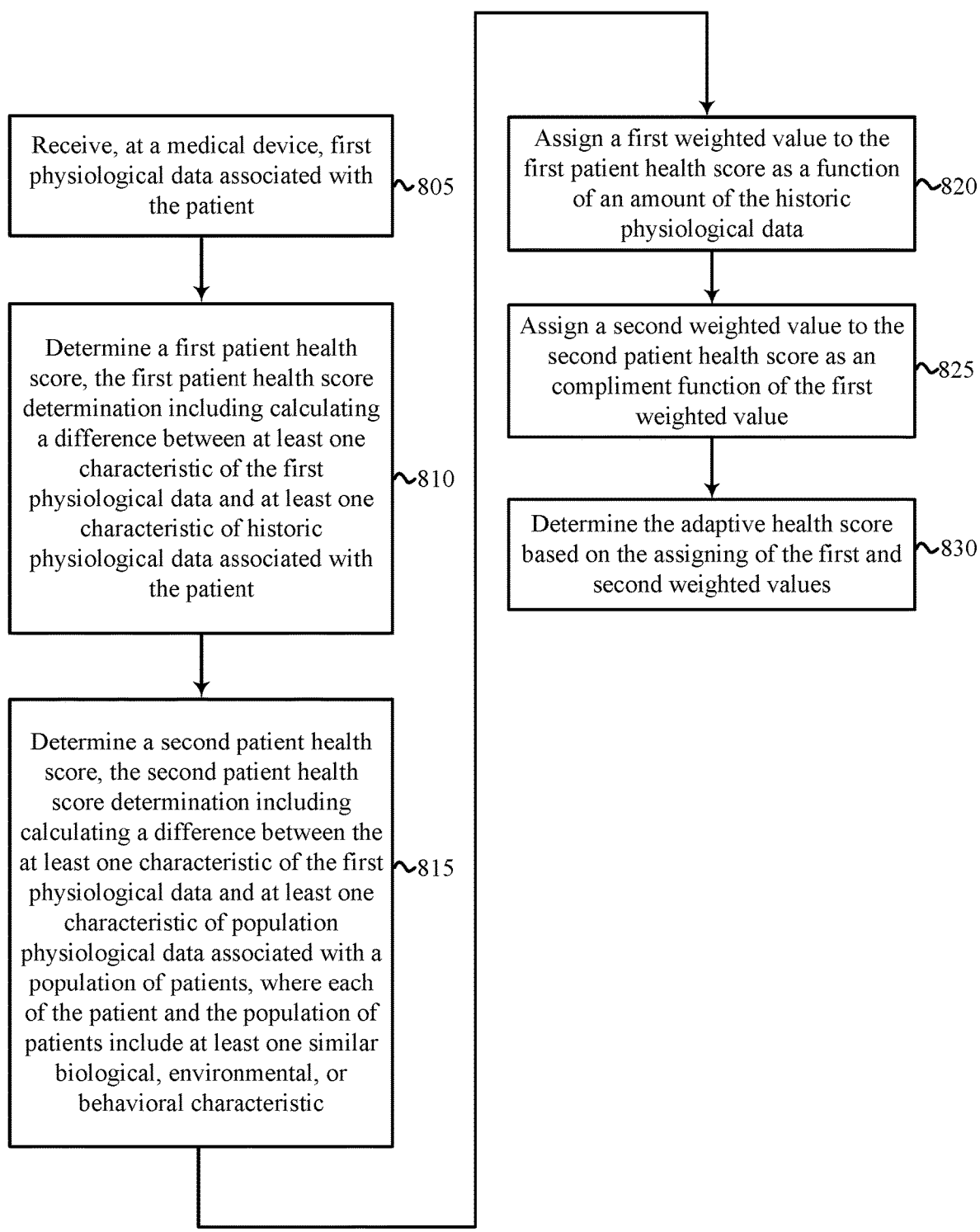
FIGS. 8 through 10 illustrate methods for adaptive health score in accordance with aspects of the present disclosure.

FIG. 8 shows a flowchart illustrating a method 800 for adaptive health score in accordance with aspects of the present disclosure. The operations of method 800 may be implemented by a medical device or its components as described herein. For example, the operations of method 800 may be performed by a health score determination component as described with reference to FIGS. 4 through 7. In some examples, a medical device may execute a set of codes to control the functional elements of the device to perform the functions described below. Additionally or alternatively, the medical device may perform aspects of the functions described below using special-purpose hardware.

At 805 the medical device may receive, at a medical device, first physiological data associated with the patient. The operations of 805 may be performed according to the methods described herein. In certain examples, aspects of the operations of 805 may be performed by a reception component as described with reference to FIGS. 4 through 7.

At 810 the medical device may determine a first patient health score, the first patient health score determination comprising calculating a difference between at least one characteristic of the first physiological data and at least one characteristic of historic physiological data associated with the patient. The operations of 810 may be performed according to the methods described herein. In certain examples, aspects of the operations of 810 may be performed by a determination component as described with reference to FIGS. 4 through 7.

At 815 the medical device may determine a second patient health score, the second patient health score determination comprising calculating a difference between the at least one characteristic of the first physiological data and at least one characteristic of population physiological data associated with a population of patients, wherein each of the patient and the population of patients comprise at least one similar biological, environmental, or behavioral characteristic. The operations of 815 may be performed according to the methods described herein. In certain examples, aspects of the operations of 815 may be performed by a determination component as described with reference to FIGS. 4 through 7.

At 820 the medical device may assign a first weighted value to the first patient health score as a function of an amount of the historic physiological data. The operations of 820 may be performed according to the methods described herein. In certain examples, aspects of the operations of 820 may be performed by an assignment component as described with reference to FIGS. 4 through 7.

At 825 the medical device may assign a second weighted value to the second patient health score as an compliment function of the first weighted value. The operations of 825 may be performed according to the methods described herein. In certain examples, aspects of the operations of 825 may be performed by an assignment component as described with reference to FIGS. 4 through 7.

At 830 the medical device may determine the adaptive health score based at least in part on the assigning of the first and second weighted values. The operations of 830 may be performed according to the methods described herein. In certain examples, aspects of the operations of 830 may be performed by a determination component as described with reference to FIGS. 4 through 7.

Figure 9:
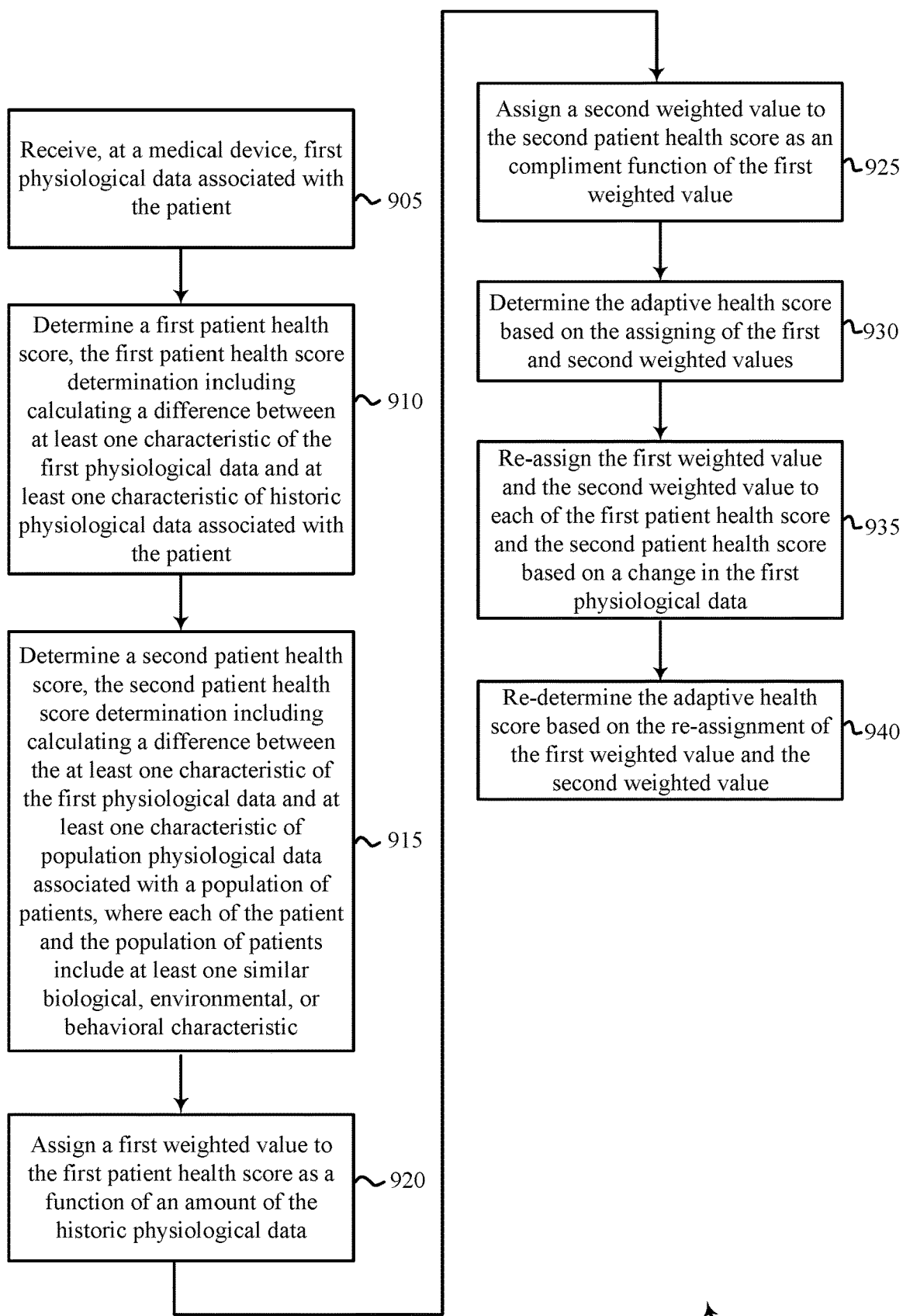

FIG. 9 shows a flowchart illustrating a method 900 for adaptive health score in accordance with aspects of the present disclosure. The operations of method 900 may be implemented by a medical device or its components as described herein. For example, the operations of method 900 may be performed by a health score determination component as described with reference to FIGS. 4 through 7. In some examples, a medical device may execute a set of codes to control the functional elements of the device to perform the functions described below. Additionally or alternatively, the medical device may perform aspects of the functions described below using special-purpose hardware.

At 905 the medical device may receive, at a medical device, first physiological data associated with the patient. The operations of 905 may be performed according to the methods described herein. In certain examples, aspects of the operations of 905 may be performed by a reception component as described with reference to FIGS. 4 through 7.

At 910 the medical device may determine a first patient health score, the first patient health score determination comprising calculating a difference between at least one characteristic of the first physiological data and at least one characteristic of historic physiological data associated with the patient. The operations of 910 may be performed according to the methods described herein. In certain examples, aspects of the operations of 910 may be performed by a determination component as described with reference to FIGS. 4 through 7.

At 915 the medical device may determine a second patient health score, the second patient health score determination comprising calculating a difference between the at least one characteristic of the first physiological data and at least one characteristic of population physiological data associated with a population of patients, wherein each of the patient and the population of patients comprise at least one similar biological, environmental, or behavioral characteristic. The operations of 915 may be performed according to the methods described herein. In certain examples, aspects of the operations of 915 may be performed by a determination component as described with reference to FIGS. 4 through 7.

At 920 the medical device may assign a first weighted value to the first patient health score as a function of an amount of the historic physiological data. The operations of 920 may be performed according to the methods described herein. In certain examples, aspects of the operations of 920 may be performed by an assignment component as described with reference to FIGS. 4 through 7.

At 925 the medical device may assign a second weighted value to the second patient health score as an compliment function of the first weighted value. The operations of 925 may be performed according to the methods described herein. In certain examples, aspects of the operations of 925 may be performed by an assignment component as described with reference to FIGS. 4 through 7.

At 930 the medical device may determine the adaptive health score based at least in part on the assigning of the first and second weighted values. The operations of 930 may be performed according to the methods described herein. In certain examples, aspects of the operations of 930 may be performed by a determination component as described with reference to FIGS. 4 through 7.

At 935 the medical device may re-assign the first weighted value and the second weighted value to each of the first patient health score and the second patient health score based at least in part on a change in the first physiological data. The operations of 935 may be performed according to the methods described herein. In certain examples, aspects of the operations of 935 may be performed by an assignment component as described with reference to FIGS. 4 through 7.

At 940 the medical device may re-determine the adaptive health score based at least in part on the re-assignment of the first weighted value and the second weighted value. The operations of 940 may be performed according to the methods described herein. In certain examples, aspects of the operations of 940 may be performed by a determination component as described with reference to FIGS. 4 through 7.

Figure 10:
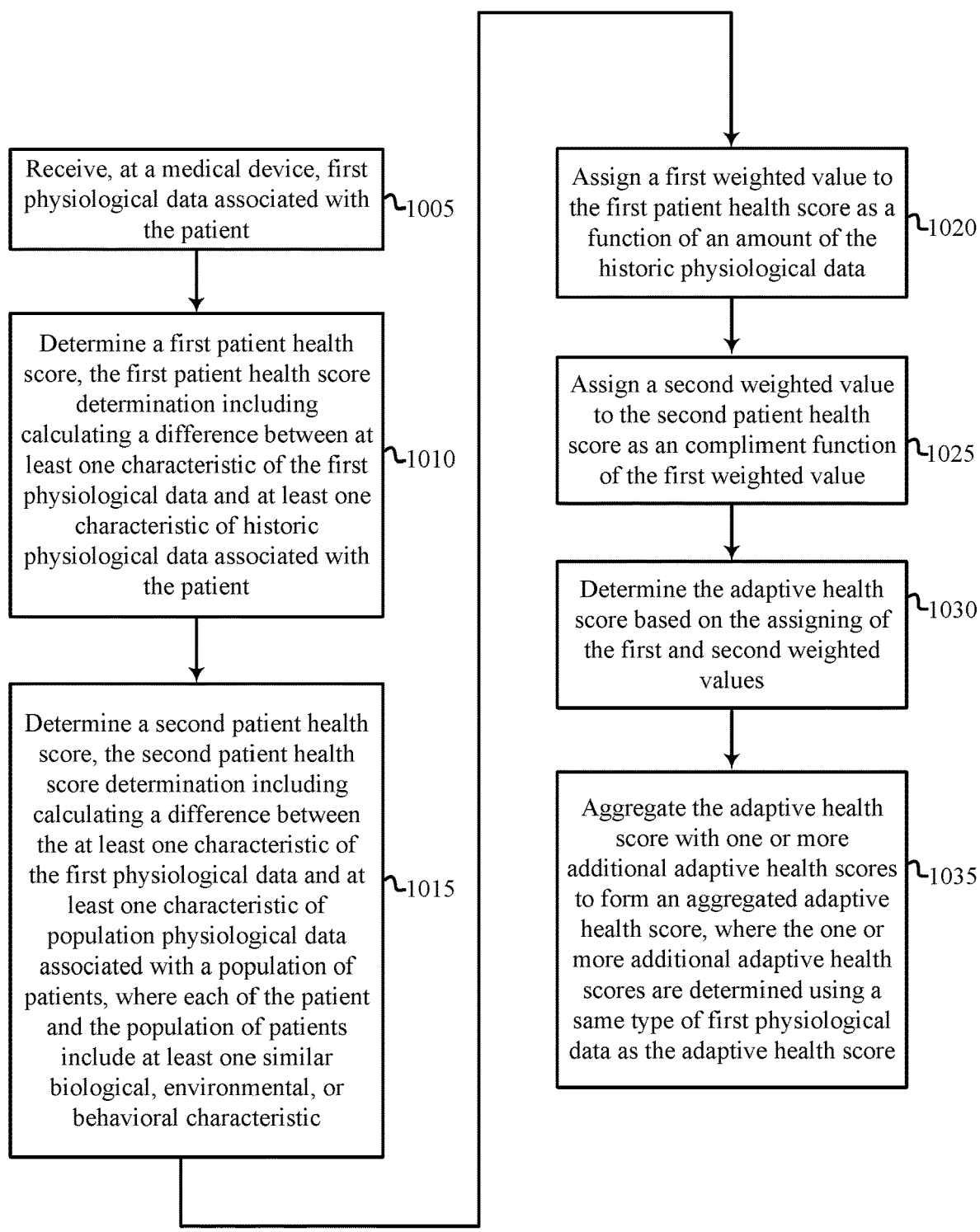

FIG. 10 shows a flowchart illustrating a method 1000 for adaptive health score in accordance with aspects of the present disclosure. The operations of method 1000 may be implemented by a medical device or its components as described herein. For example, the operations of method 1000 may be performed by a health score determination component as described with reference to FIGS. 4 through 7. In some examples, a medical device ### may execute a set of codes to control the functional elements of the device to perform the functions described below. Additionally or alternatively, the medical device may perform aspects of the functions described below using special-purpose hardware.

At 1005 the medical device may receive, at a medical device, first physiological data associated with the patient. The operations of 1005 may be performed according to the methods described herein. In certain examples, aspects of the operations of 1005 may be performed by a reception component as described with reference to FIGS. 4 through 7.

At 1010 the medical device may determine a first patient health score, the first patient health score determination comprising calculating a difference between at least one characteristic of the first physiological data and at least one characteristic of historic physiological data associated with the patient. The operations of 1010 may be performed according to the methods described herein. In certain examples, aspects of the operations of 1010 may be performed by a determination component as described with reference to FIGS. 4 through 7.

At 1015 the medical device may determine a second patient health score, the second patient health score determination comprising calculating a difference between the at least one characteristic of the first physiological data and at least one characteristic of population physiological data associated with a population of patients, wherein each of the patient and the population of patients comprise at least one similar biological, environmental, or behavioral characteristic. The operations of 1015 may be performed according to the methods described herein. In certain examples, aspects of the operations of 1015 may be performed by a determination component as described with reference to FIGS. 4 through 7.

At 1020 the medical device may assign a first weighted value to the first patient health score as a function of an amount of the historic physiological data. The operations of 1020 may be performed according to the methods described herein. In certain examples, aspects of the operations of 1020 may be performed by an assignment component as described with reference to FIGS. 4 through 7.

At 1025 the medical device may assign a second weighted value to the second patient health score as an compliment function of the first weighted value. The operations of 1025 may be performed according to the methods described herein. In certain examples, aspects of the operations of 1025 may be performed by an assignment component as described with reference to FIGS. 4 through 7.

At 1030 the medical device may determine the adaptive health score based at least in part on the assigning of the first and second weighted values. The operations of 1030 may be performed according to the methods described herein. In certain examples, aspects of the operations of 1030 may be performed by a determination component as described with reference to FIGS. 4 through 7.

At 1035 the medical device may aggregate the adaptive health score with one or more additional adaptive health scores to form an aggregated adaptive health score, wherein the one or more additional adaptive health scores are determined using a same type of first physiological data as the adaptive health score. The operations of 1035 may be performed according to the methods described herein. In certain examples, aspects of the operations of 1035 may be performed by a aggregation component as described with reference to FIGS. 4 through 7.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing front the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for determining an adaptive health score associated with a patient, comprising:
   measuring, at one or more sensors of a medical device coupled with the patient, first physiological data and second physiological data associated with the patient;

transmitting, from the medical device and to a central station, the first physiological data based at least in part on measuring the first physiological data;

receiving, at the central station and from the medical device, the first physiological data associated with the patient;

displaying, at the central station, the first physiological data associated with the patient;

determining, at the central station, a first patient health score, the first patient health score determination comprising calculating a difference between at least one characteristic of the first physiological data and at least one characteristic of historic physiological data associated with the patient;

determining, at the central station, a second patient health score, the second patient health score determination comprising calculating a difference between the at least one characteristic of the first physiological data and at least one characteristic of population physiological data associated with a population of patients, wherein each of the patient and the population of patients comprise at least one similar biological, environmental, or behavioral characteristic;

assigning, at the central station, a first weighted value to the first patient health score as a function of an amount of the historic physiological data, wherein the assigned first weighted value is increased as the amount of the historic physiological data increases;

assigning, at the central station, a second weighted value to the second patient health score as a compliment function of the first weighted value;

determining, at the central station, the adaptive health score based at least in part on the assigning of the first and second weighted values;

re-assigning, at the central station, the first weighted value and the second weighted value to each of the first patient health score and the second patient health score based at least in part on a change in the first physiological data;

re-determining, at the central station, the adaptive health score based at least in part on the re-assignment of the first weighted value and the second weighted value; and displaying, at the central station, the adaptive health score based at least in part on re-determining the adaptive health score.

2. The method of claim 1, further comprising:
receiving the first physiological data associated with the patient at a first time; and
receiving the first physiological data associated with the patient at a second time different from the first time, wherein the re-assignment of the weighted value to the first patient health score and the second patient health score is based at least in part on a change in the first physiological data from the first time to the second time.

3. The method of claim 1, further comprising:
transmitting, from the medical device and to the central station, the second physiological data based at least in part on measuring the second physiological data; and
receiving, at the central station, the second physiological data associated with the patient that is different from the first physiological data, wherein the determination of the first patient health score and the second patient health score are based at least in part on the second physiological data received.

4. The method of claim 1, wherein the adaptive health score is a weighted average of the first patient health score and the second patient health score.

5. The method of claim 1, wherein the at least one similar biological, environmental, or behavioral characteristic comprises an age, a gender, a height, a weight, an activity level, a patient demographic, a patient posture, or a combination thereof of each of the patient and the population of patients.

6. The method of claim 1, wherein the first physiological data comprises heart rate information.

7. The method of claim 1, wherein the first physiological data associated with the patient is continually received at the central station.

8. The method of claim 1, wherein a frequency of receiving the first physiological data is based at least in part on a type of the first physiological data.

9. The method of claim 1, further comprising:
aggregating the adaptive health score with one or more additional adaptive health scores to form an aggregated adaptive health score, wherein the one or more additional adaptive health scores are determined using a same type of the first physiological data as the adaptive health score.

10. A system for determining an adaptive health score associated with a patient, comprising:
one or more processors;
memory in electronic communication with the one or more processors; and
instructions stored in the memory and executable by the one or more processors to cause a medical device and a central station to:
measure, at one or more sensors of the medical device coupled with the patient, first physiological data and second physiological data associated with the patient;
transmit, from the medical device and to the central station, the first physiological data based at least in part on measuring the first physiological data;
receive, at the central station and from the medical device, the first physiological data associated with the patient;
display, at the central station, the first physiological data associated with the patient;
determine, at the central station, a first patient health score, the first patient health score determination comprising calculating a difference between at least one characteristic of the first physiological data and at least one characteristic of historic physiological data associated with the patient;
determine, at the central station, a second patient health score, the second patient health score determination comprising calculating a difference between the at least one characteristic of the first physiological data and at least one characteristic of population physiological data associated with a population of patients, wherein each of the patient and the population of patients comprise at least one similar biological, environmental, or behavioral characteristic;
assign, at the central station, a first weighted value to the first patient health score as a function of an amount of the historic physiological data, wherein the assigned first weighted value is increased as the amount of the historic physiological data increases;
assign, at the central station, a second weighted value to the second patient health score as a compliment function of the first weighted value;
determine, at the central station, the adaptive health score based at least in part on the assigning of the first and second weighted values;

re-assign, at the central station, the first weighted value and the second weighted value to each of the first patient health score and the second patient health score based at least in part on a change in the first physiological data;

re-determine, at the central station, the adaptive health score based at least in part on the re-assignment of the first weighted value and the second weighted value; and display, at the central station, the adaptive health score based at least in part on re-determining the adaptive health score.

11. The system of claim 10, wherein the instructions are further executable by the one or more processors to cause the central station to:

receive the first physiological data associated with the patient at a first time; and receive the first physiological data associated with the patient at a second time different from the first time, wherein the re-assignment of the weighted value to the first patient health score and the second patient health score is based at least in part on a change in the first physiological data from the first time to the second time.

12. One or more non-transitory computer-readable media storing code for determining an adaptive health score associated with a patient, the code comprising instructions executable by one or more processors to:

measure, at one or more sensors of a medical device coupled with the patient, first physiological data and second physiological data associated with the patient;

transmit, from the medical device and to a central station, the first physiological data based at least in part on measuring the first physiological data;

receive, at the central station and from the medical device, the first physiological data associated with the patient;

display, at the central station, the first physiological data associated with the patient;

determine, at the central station, a first patient health score, the first patient health score determination comprising calculating a difference between at least one characteristic of the first physiological data and at least one characteristic of historic physiological data associated with the patient;

determine, at the central station, a second patient health score, the second patient health score determination comprising calculating a difference between the at least one characteristic of the first physiological data and at least one characteristic of population physiological data associated with a population of patients, wherein each of the patient and the population of patients comprise at least one similar biological, environmental, or behavioral characteristic;

assign, at the central station, a first weighted value to the first patient health score as a function of an amount of the historic physiological data, wherein the assigned first weighted value is increased as the amount of the historic physiological data increases;

assign, at the central station, a second weighted value to the second patient health score as a compliment function of the first weighted value;

determine, at the central station, the adaptive health score based at least in part on the assigning of the first and second weighted values;

re-assign, at the central station, the first weighted value and the second weighted value to each of the first patient health score and the second patient health score based at least in part on a change in the first physiological data;

re-determine, at the central station, the adaptive health score based at least in part on the re-assignment of the first weighted value and the second weighted value; and display, at the central station, the adaptive health score based at least in part on re-determining the adaptive health score.

* * * * *